(12) United States Patent
Ward et al.

(10) Patent No.: US 6,860,856 B2
(45) Date of Patent: Mar. 1, 2005

(54) ECHOGENIC SURFACE FOR ENHANCED ULTASONIC VISIBILITY

(75) Inventors: Tim E. Ward, Bedford, IN (US); Mark Mallaby, Indianapolis, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/045,986

(22) Filed: Jan. 11, 2002

(65) Prior Publication Data

US 2003/0135117 A1 Jul. 17, 2003

(51) Int. Cl.[7] .................................................. A61B 8/14
(52) U.S. Cl. ...................................................... 600/459
(58) Field of Search .............................. 600/407–471; 606/130; 601/2, 3, 4; 607/122; 128/898, 916; 367/7, 11; 73/625, 626

(56) References Cited

U.S. PATENT DOCUMENTS

| | | | |
|---|---|---|---|
| 4,401,124 A | 8/1983 | Guess et al. ................ 128/660 |
| 4,582,061 A | 4/1986 | Fry ........................ 128/329 R |
| 4,869,259 A | 9/1989 | Elkins ........................ 128/660 |
| 5,048,530 A | 9/1991 | Hurwitz .................. 128/662.05 |
| 5,289,831 A | 3/1994 | Bosley | |
| 5,383,466 A | 1/1995 | Partika .................. 128/662.03 |
| 5,490,521 A | 2/1996 | Davis .................... 128/662.02 |
| 5,766,135 A | * 6/1998 | Terwilliger ................. 600/567 |
| 5,769,795 A | * 6/1998 | Terwilliger ................. 600/567 |
| 5,820,554 A | * 10/1998 | Davis et al. ................ 600/431 |
| 6,018,676 A | 1/2000 | Davis et al. | |

FOREIGN PATENT DOCUMENTS

| | | |
|---|---|---|
| EP | 1 132 049 A1 | 9/2001 |
| GB | 2 298 368 A | 9/1996 |

* cited by examiner

*Primary Examiner*—Ali Imam
(74) *Attorney, Agent, or Firm*—Orrick, Herrington & Sutcliffe LLP

(57) ABSTRACT

An improved medical device, such as a needle, has a surface which enhances the "echogenicity" or ultrasound visibility of the medical device so that the medical device can be guided inside a human body using ultrasound imaging. In one embodiment, concave slots are formed on the surface of the improved medical device to enhance the ultrasound visibility of the improved medical device. The surface of each concave slot is substantially flat in a radial cross section of the needle and curved in an axial cross section of the improved medical device.

41 Claims, 4 Drawing Sheets

US 6,860,856 B2

ECHOGENIC SURFACE FOR ENHANCED ULTASONIC VISIBILITY

BACKGROUND OF THE INVENTION

1. Field of the Invention

The field of the invention relates generally to echogenic surfaces, and more particularly, to echogenic surfaces for medical instruments, e.g., needles used in medical procedures, to enhance the ultrasonic visibility of the medical instruments.

2. Background

Needles are commonly used in various medical procedures, such as biopsy and amniocentesis procedures, to gain percutaneous access into the body. In a biopsy, for example, a biopsy needle is inserted into the body to collect a tissue sample from a tumor. In amniocentesis, an aspiration needle is inserted into the amniotic sac to collect amniotic fluid.

These medical procedures are frequently monitored using an imaging technique. One widely used imaging technique is ultrasonography, which is commonly used to image the development of a fetus. Ultrasonography relies on the "echogenicity" or ultrasonic visibility of organs and bones, and medical instruments placed inside the body. In a biopsy, ultrasonography is used to guide the biopsy needle to the tumor site. In amniocentesis, ultrasonography is used to guide the aspiration needle inside the amniotic sac to avoid injury to the fetus.

In order to guide a needle inside the body using ultrasonography, the needle must be visible in an ultrasound image. Unfortunately, the smooth cylindrical surface of a needle is very difficult to image using ultrasonography. FIG. 1 illustrates a medical device 20 (e.g., a needle) of the prior art shows ultrasound waves 10 emitted from a transducer 15 striking the surface of the device 20. The device 20 reflects the ultrasound waves 10 in a direction 25 away from the transducer 15. As a result, the emitted ultrasound waves 10 are not returned to the transducer 15 and the device 20 is not imaged.

To address this problem, various methods have been developed to enhance the "echogenicity" or ultrasonic visibility of a medical device, which problem can be worse for a thin device such as a needle. These methods typically involve providing a disrupted surface at the distal end or tip of the medical device or needle to enhance its ultrasonic visibility. Current methods for providing disrupted surfaces on a needle include forming rings around the outer and/or inner cannula of the needle, sandblasting the needle surface, chemically etching the needle surface, drilling holes through the cannula of the needle, and coating the needle surface with a polymeric coating. The resulting disrupted surfaces enhance the ultrasonic visibility of the needle by isotropically scattering incident ultrasonic waves. FIG. 2 illustrates an example of a prior art needle 30 with a disrupted surface 35 at its distal end. FIG. 2 shows ultrasound waves 10 emitted from a transducer 15 striking the disrupted surface 35 of the needle 30. The disrupted surface 35 reflects the ultrasound waves 10 in random directions 40 with some of the waves being reflected back to the transducer 15 and some of the waves being reflected away from the transducer 15. The reflected waves received by the transducer 15 are used to create an ultrasound image of the needle.

Another method to enhance the ultrasonic visibility of a needle is to form dimples on the needle surface. FIG. 3A illustrates a side view of a prior art needle 50 with dimples 55 formed along its surface. FIG. 3B shows a radial cross sectional view of the prior art needle 50 of FIG. 3A. FIG. 3B shows ultrasound waves 65 striking one of the dimples 55 from a transducer 60. The dimples 55 reflect the ultrasound waves in different directions 70 with some of the waves being reflected back to the transducer 60 to form an ultrasound image and some of the waves being reflected away from the transducer 60.

Although the usefulness of etched, coated and sandblasted surfaces has been demonstrated, these disrupted surfaces typically have random disruptions that scatter incident ultrasound waves with no real direction. In addition, the dimples 55 only direct ultrasound waves that are reflected off of a single point on its surface back to the transducer. The rest of the ultrasound waves are directed away from the transducer.

Therefore, there is a need for an echogenic surface that reflects more of the ultrasound waves back to the transducer. Such an echogenic surface would provide improved ultrasonic visibility of medical instruments, such as needles. This would make it easier for physicians to guide the medical instruments inside the body using ultrasonography.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
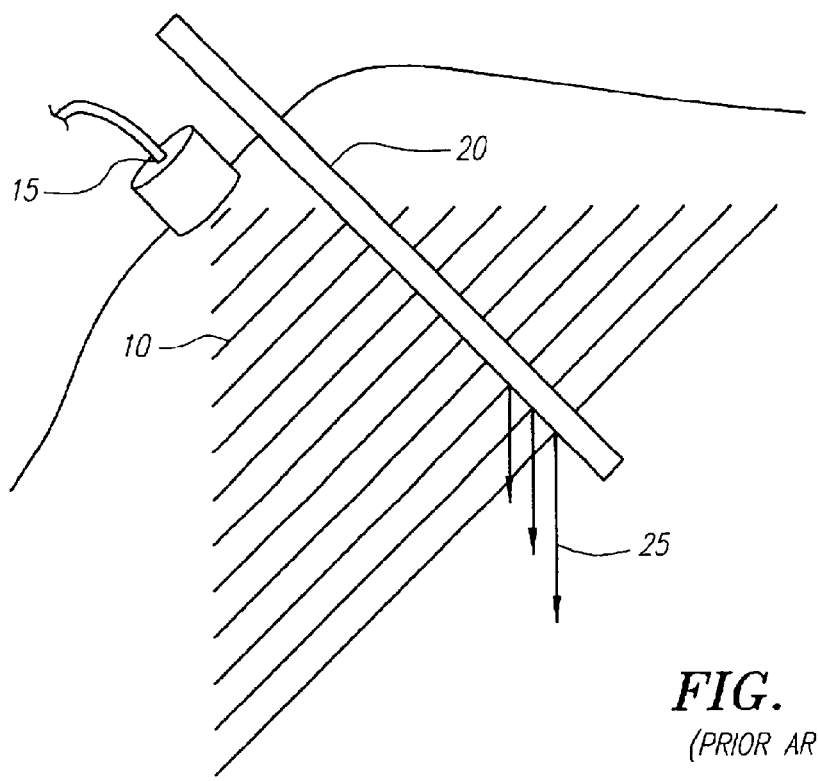
FIG. 1 is an illustration of a prior art needle having a smooth surface and shows ultrasound waves from a transducer striking the needle.
Figure 2:
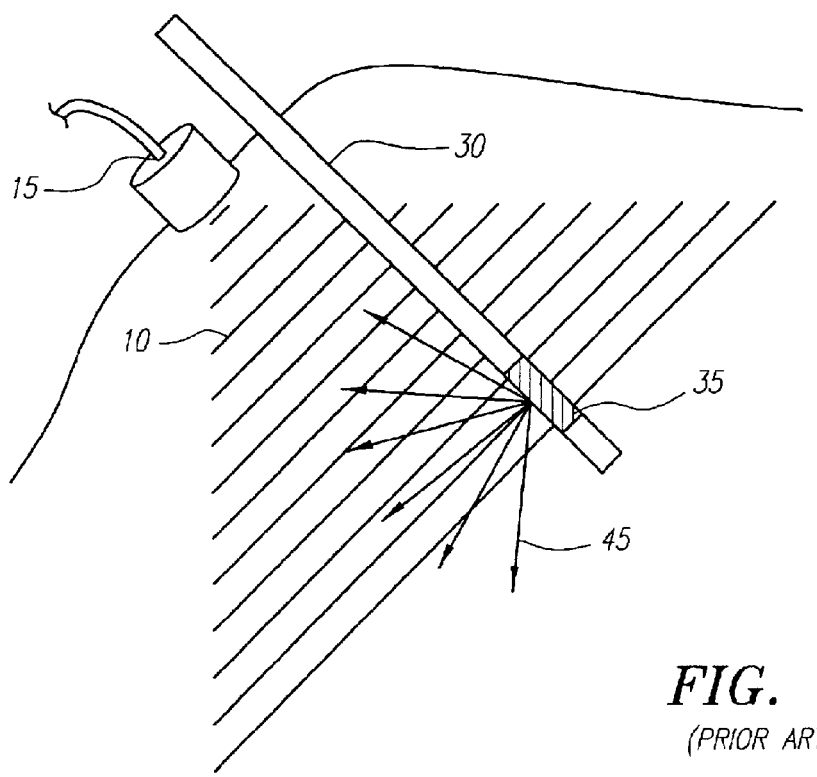
FIG. 2 is an illustration of a prior art needle having a disrupted surface at its distal end and shows ultrasound waves from a transducer striking the needle
Figure 3A:
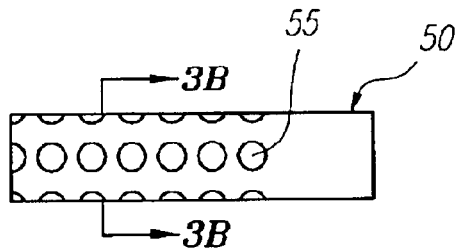
FIG. 3A is a side view of a prior art needle with dimples formed along its surface.
Figure 3B:
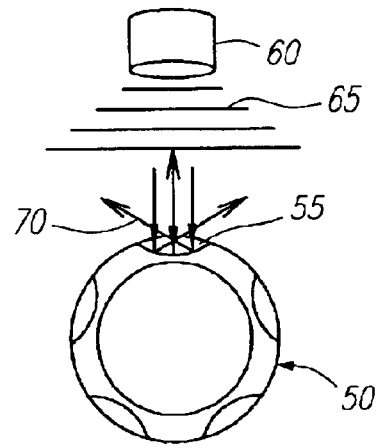
FIG. 3B is a radial cross section of the prior art needle in FIG. 3A.
Figure 4A:
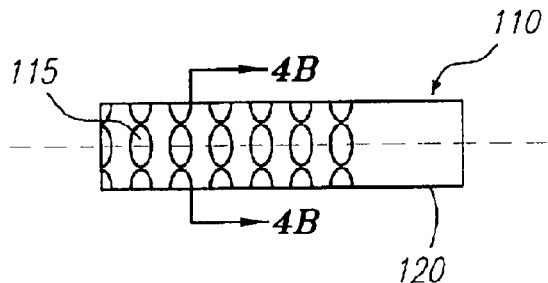
FIG. 4A is a schematic illustration of a side view of an improved medical device with concave slots formed on the surface of the needle.

FIG. 4A is a schematic illustration of a side view of an improved medical device 110 with concave slots 115 formed on the surface 120 of the medical device 110. The improved medical device 110 may be any device intended for use within a human body such as a needle or catheter. In order to demonstrate an example, the improved medical device 110 may be referred to as a needle. However, references to any of the improved medical devices as a "needle" should not be construed to limit the medical device to needles.

The surface 120 may be made of the same or different material as the rest of the improved medical device 110. The surface 120 may be, for example, stainless steel or plastic. The concave slots 115 preferably are located near or at the location of the improved medical device 110 which the physician desires to image. Thus, for a needle, the concave slots 115 may be located near the distal end or tip of the needle. The concave slots 115 may be formed on the surface 120 of the needle 110 using a variety of techniques, including drilling, milling, etching, or pressing.

Figure 4B:
FIG. 4B is a schematic illustration of a radial cross sectional view of the medical device in FIG. 4A.
Figure 4B:
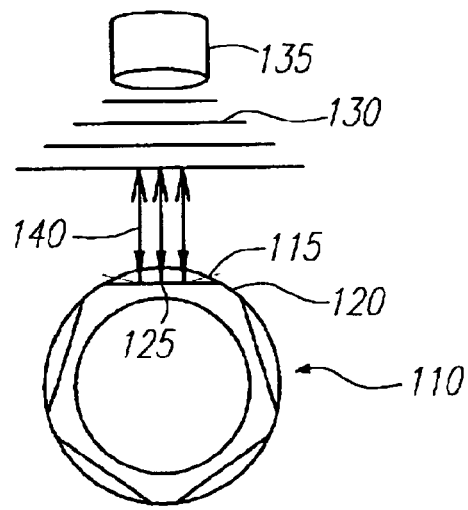

FIG. 4B is a schematic illustration of a radial cross sectional view of the improved medical device 110 of FIG. 4A. The surface of each concave slot 115 is substantially flat or straight 125 in the radial cross section. As shown in FIG. 4B, ultrasound waves 130 strike the flat surface 125 of one of the concave slots 115 from a transducer 135 that is aligned with the flat surface 125. The ultrasound waves 130 are reflected off of the entire flat surface 125 of the concave slot 115 in a direction 140 back to the transducer 135. In contrast, the dimple 55 of the prior art only reflects ultrasound waves off of a single point on its surface back to the transducer, with the rest of the ultrasound waves being reflected away form the transducer. Thus, the concave slots 115 of the improved medical device are able to reflect more of the ultrasound waves of the transducer 135 back to the transducer 135 than dimples 50, thereby providing a brighter and less interrupted ultrasound image.

Figure 4C:
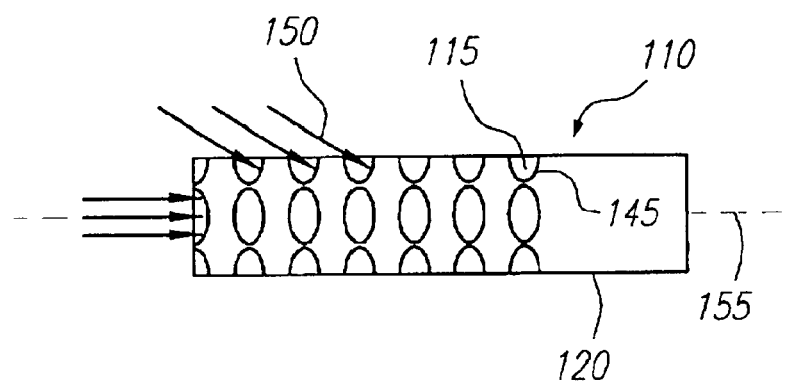
FIG. 4C is a schematic illustration of an exploded side view of the medical device in FIG. 4A.

FIG. 4C is a schematic illustration of an exploded side view of the improved medical device 110 of FIGS. 4A and 4B. Each concave slot 115 has a curved surface 145 in the axial cross section. The curved surface 145 may be hemispherical, oval, or the like. The curved surface 145 of each concave slot 115 in the axial cross section enables the concave slot 115 to reflect "off axis" ultrasound waves 150 back to the transducer. The "off angle" ultrasound waves 150 are ultrasound waves that approach the concave slot 115 at an angle with respect to the axis 155 of the improved medical device 110. By increasing the curvature of the curved surface 145, each concave slot 115 is able to reflect "off axis" ultrasound waves 150 at more acute (i.e., steeper) angles with respect to the axis 155 of the improved medical device 110. This feature is desirable when the transducer becomes orientated at an acute angle with respect to the axis 155 of the improved medical device 110, which can occur as the improved medical device 110 is inserted deeper into a human body.

Therefore, the concave slot 115 of the improved medical device has a flat surface 125 in the radial cross section of the needle 110 and a curved surface 145 in the axial cross section of the needle 110. The flat surface 125 in the radial cross section enables the concave slot 115 to reflect more of the ultrasound waves back to the transducer, while the curved surface 145 in the axial cross section enables the concave slot 115 to reflect "off axis" ultrasound waves back to the transducer.

Referring to FIG. 4A, the concave slots 115 are arranged preferably along the entire circumference of the needle 110. This enables the needle 110 to be visualized regardless of the rotational orientation of the needle 110 with respect to the transducer.

Figure 5:
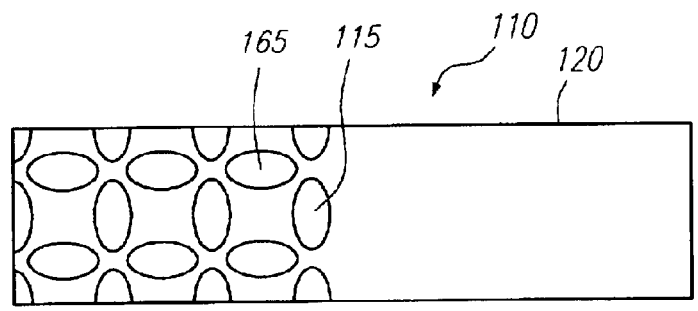
FIG. 5 is a schematic illustration of an example arrangement of concave slots formed on the surface of the improved medical device.

FIG. 5 is a schematic illustration of another example embodiment of the improved medical device 110 in which concave slots are arranged in a different pattern on the surface 120 of the improved medical device 110. Some of the concave slots 115 are orientated in the same direction as in the example embodiment illustrated in FIGS. 4A–4C, in which the concave slots 115 have a flat surface in the radial cross section and a curved surface in the axial cross section of the improved medical device 110. The rest of the concave slots 165, however, are orientated in a perpendicular direction, in which the surface of the concave slots 165 is flat in the axial cross section and curved in the radial cross section. By arranging the concave slots 115 and 165 in two different orientations on the surface 110 of the improved medical device 110, the improved medical device 110 is able to reflect ultrasound waves from different angles of approach back to the transducer. This increases flexibility by allowing the improved medical device 110 to be visualized from different angles of entry into a body in relation to the transducer.

Figure 6:
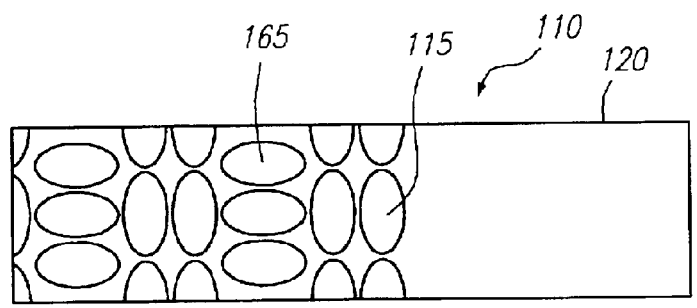
FIG. 6 is a schematic illustration of another example arrangement of concave slots formed on the surface of the improved medical device.

FIG. 6 is a schematic illustration of still another example arrangement of the concave slots 115 and 165 on the surface of an improved medical device. The concave slots 115 and 165 may be arranged in a variety of patterns on the needle to achieve different image responses for the improved medical device. In addition, the concave slots may be arranged in different orientations on the improved medical device other than those shown in FIGS. 5 and 6 to reflect ultrasound waves from various angles back to the transducer. In this case, the surface of each concave slot is flat in one cross section and curved in a perpendicular cross section.

Figure 7:
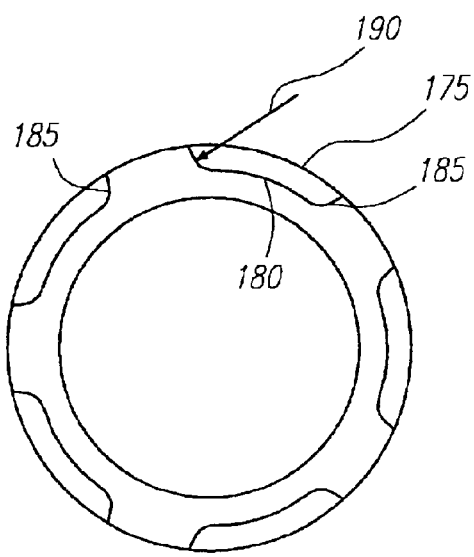
FIG. 7 is a schematic illustration of a radial cross sectional view of another example embodiment of an improved medical device having concave slots formed on the surface of the medical device.

FIG. 7 is a schematic illustration of a radial cross sectional view of yet another example of an improved medical device having concave slots 175. Each concave slot 175 has a bottom surface 180 that follows the contour of the surface of the improved medical device, such as a needle. In the example shown in FIG. 7, the bottom surface 180 of each concave slot 175 is convex to follow the cylindrical contour of the surface of the improved medical device. Each concave slot 175 has curved side surfaces 185 on each end of the bottom surface 180. The curved side surfaces 185 reflect ultrasound waves back to the transducer when the ultrasound waves 190 approach the concave slot 175 from skewed (i.e., sideways) angles with respect to the concave slot 175. The curved side surfaces 185 may be concave, for example.

While various embodiments of the application have been described, it will be apparent to those of ordinary skill in the art that many more embodiments and implementations are possible that are within the scope of the subject invention. For example, each feature of one embodiment can be mixed and matched with other features shown in other embodiments. Additionally, the invention may be applied to the surface of other medical instruments besides needles where it is desirable to enhance the ultrasonic visibility of such instruments. For example, the invention may be applied to the surface of a catheter to enhance the ultrasonic visibility of the catheter. Therefore, the invention is not to be restricted or limited except in accordance with the following claims and their equivalents.

What is claimed is:

1. A medical device, comprising:
    an elongate body;
    a plurality of elongate slots formed on the elongate body, wherein a portion of at least one slot extends along a straight line axis and has a first substantially concave sidewall.

2. The medical device of claim 1, wherein the body has a longitudinal axis and the straight line axis is transverse to the longitudinal axis.

3. The medical device of claim 2, wherein the straight line axis is perpendicular to the longitudinal axis.

4. The medical device of claim 3, wherein the entire slot extends along a straight line axis.

5. The medical device of claim 1, wherein the entire slot extends along a straight line axis.

6. The medical device of claim 1, further comprising a second substantially concave sidewall.

7. The medical device of claim 6, wherein the body has a longitudinal axis and the straight line axis is transverse to the longitudinal axis.

8. The medical device of claim 7, wherein the straight line axis is perpendicular to the longitudinal axis.

9. The medical device of claim 8, wherein the entire slot extends along a straight line axis.

10. The medical device of claim 1, wherein at the substantially concave sidewall has a uniform degree of curvature.

11. The medical device of claim 1, wherein the at least one slot has a first end and a second end and extends along the straight line axis therebetween.

12. The medical device of claim 1, wherein the plurality of slots are located radially about the body.

13. The medical device of claim 1, wherein the plurality of slots are located axially along the body.

14. The medical device of claim 1, wherein at least two of the plurality of slots are located radially about the body, and wherein at least two of the plurality of slots are located axially along the body.

15. The medical device of claim 1, wherein the plurality of slots are formed in a stainless steel portion of the elongated body.

16. The medical device of claim 1, wherein the plurality of concave slots are formed in a plastic portion of the elongated body.

17. The medical device of claim 1, wherein the medical device is a needle.

18. The medical device of claim 1, wherein the medical device is a catheter.

19. The medical device of claim 1, wherein at least one of the plurality of slots has a first and a second substantially concave sidewall located on opposite sides of a substantially convex bottom portion, wherein the bottom portion extends along a straight line axis.

20. The medical device of claim 19, wherein the slot further comprises a first and a second endwall opposing each other.

21. The medical device of claim 20, wherein at least one endwall is substantially concave.

22. A medical device, comprising:
an elongate body;
a plurality of elongate slots formed on the elongate body, wherein at least one of the plurality of slots has a first substantially concave sidewall located on a first side of a substantially convex bottom portion, wherein the bottom portion extends along a straight line axis.

23. The medical device of claim 22, wherein the body has a longitudinal axis and the straight line axis is parallel to the longitudinal axis.

24. The medical device of claim 22, wherein the substantially concave sidewall has a uniform degree of curvature.

25. The medical device of claim 24, wherein the slot further comprises a second substantially concave sidewall located on a second side of the substantially convex bottom portion, wherein the second side is opposite the first.

26. The medical device of claim 25, wherein the slot further comprises a first and a second endwall opposing each other.

27. The medical device of claim 26, wherein at least one endwall is substantially concave.

28. The medical device of claim 22, wherein the plurality of slots are located radially about the body.

29. The medical device of claim 22, wherein the plurality of slots are located axially along the body.

30. The medical device of claim 22, wherein at least two of the plurality of slots are located radially about the body, and wherein at least two of the plurality of slots are located axially along the body.

31. The medical device of claim 22, wherein the plurality of slots are formed in a stainless steel portion of the elongated body.

32. The medical device of claim 22, wherein the plurality of concave slots are formed in a plastic portion of the elongated body.

33. The medical device of claim 22, wherein the medical device is a needle.

34. The medical device of claim 22, wherein the medical device is a catheter.

35. The medical device of claim 22, wherein a portion of a second slot extends along a second straight line axis and has two substantially concave sidewalls.

36. The medical device of claim 35, wherein the body has a longitudinal axis and the second straight line axis is transverse to the longitudinal axis.

37. The medical device of claim 36, wherein the second straight line axis is perpendicular to the longitudinal axis.

38. The medical device of claim 37, wherein the entire slot extends along a straight line axis.

39. The medical device of claim 35, wherein the entire slot extends along a straight line axis.

40. The medical device of claim 35, wherein at least one of the substantially concave sidewalls of the second slot has a uniform degree of curvature.

41. The medical device of claim 35, wherein the second slot has a first end and a second end and extends along the second straight line axis therebetween.

* * * * *